United States Patent
Wood et al.

(10) Patent No.: US 7,842,021 B2
(45) Date of Patent: Nov. 30, 2010

(54) ABSORBENT ARTICLE WITH SEAL AND METHOD OF MANUFACTURING

(75) Inventors: Leigh E. Wood, Woodbury, MN (US); Randall L. Alberg, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 989 days.

(21) Appl. No.: 11/457,635

(22) Filed: Jul. 14, 2006

(65) Prior Publication Data

US 2007/0293840 A1    Dec. 20, 2007

Related U.S. Application Data

(63) Continuation-in-part of application No. 11/423,977, filed on Jun. 14, 2006.

(51) Int. Cl.
  *A61F 13/15* (2006.01)
  *B27D 1/08* (2006.01)

(52) U.S. Cl. .............. 604/385.201; 604/385.3; 604/385.101; 604/378; 604/379; 604/385.01; 156/204; 156/226; 156/227; 156/222

(58) Field of Classification Search .......... 604/385.201, 604/385.01, 385.24, 385.3, 385.101, 378, 604/379; 156/204, 226, 227, 222
See application file for complete search history.

(56) References Cited

U.S. PATENT DOCUMENTS

| | | |
|---|---|---|
| 3,860,003 A | 1/1975 | Buell |
| 3,881,491 A | 5/1975 | Whyte |
| 3,921,232 A | 11/1975 | Whyte |
| 4,421,501 A | 12/1983 | Scheffer |
| 4,488,927 A | 12/1984 | Hooper |
| 4,515,595 A | 5/1985 | Kievit et al. |
| 4,578,070 A | 3/1986 | Holtman |
| 4,610,678 A | 9/1986 | Weisman et al. |
| 4,614,512 A | 9/1986 | Capdeboscq |
| 4,673,402 A | 6/1987 | Weisman et al. |
| 4,681,580 A | 7/1987 | Reising et al. |
| 4,682,977 A | 7/1987 | Buxton |
| RE32,649 E | 4/1988 | Brandt et al. |
| 4,753,646 A * | 6/1988 | Enloe .................. 604/385.29 |
| 4,834,735 A | 5/1989 | Alemany et al. |
| 4,904,251 A | 2/1990 | Igaue et al. |
| 4,916,005 A | 4/1990 | Lippert et al. |

(Continued)

FOREIGN PATENT DOCUMENTS

CA    2146065 A1    10/1996

(Continued)

*Primary Examiner*—Jacqueline F. Stephens

(57) ABSTRACT

Absorbent articles with waist seals are disclosed. The seals are formed from folded stacks, discrete segments, or pleated material arranged to provide a resiliently compressible seal that can be located at one or more locations within the absorbent article, e.g., along a central portion of the rear waist region of a diaper. The seals may be constructed from relatively thin materials that (through folding, stacking, pleating, etc.) can provide a resiliently compressible seal that is thick enough and appropriately shaped to conform to the wearer's anatomy well enough to provide the desired sealing. At the same, time, the continuous web material used to form the seal is preferably thin enough to be economically delivered to the manufacturing line in roll form. The seals may be provided in the form of compressed seals that expand when one or more openings are formed in a sealed cavity containing compressed resilient material.

15 Claims, 6 Drawing Sheets

U.S. PATENT DOCUMENTS

| | | | |
|---|---|---|---|
| 4,938,754 A | 7/1990 | Mesek | |
| 4,965,122 A | 10/1990 | Morman | |
| 4,978,570 A | 12/1990 | Heyn et al. | |
| 4,981,747 A | 1/1991 | Morman | |
| 5,007,890 A | 4/1991 | Alverth et al. | |
| 5,064,421 A | 11/1991 | Tracy | |
| 5,112,326 A | 5/1992 | Quadrini | |
| 5,147,345 A | 9/1992 | Young et al. | |
| 5,151,092 A | 9/1992 | Buell et al. | |
| 5,188,626 A | 2/1993 | Toyoda et al. | |
| 5,217,445 A | 6/1993 | Young et al. | |
| 5,234,423 A | 8/1993 | Alemany et al. | |
| 5,300,007 A | 4/1994 | Kober | |
| 5,300,055 A | 4/1994 | Buell | |
| 5,324,277 A | 6/1994 | Daugan et al. | |
| 5,330,459 A | 7/1994 | Lavon et al. | |
| 5,435,806 A | 7/1995 | Daugan et al. | |
| 5,520,674 A | 5/1996 | Lavon et al. | |
| 5,531,730 A | 7/1996 | Dreier | |
| 5,556,360 A | 9/1996 | Kober et al. | |
| 5,558,660 A | 9/1996 | Dreier | |
| 5,582,604 A | 12/1996 | Ahr et al. | |
| 5,601,545 A | 2/1997 | Glaug et al. | |
| 5,628,741 A | 5/1997 | Buell et al. | |
| 5,643,241 A | 7/1997 | Ahr et al. | |
| 5,772,649 A | 6/1998 | Siudzinski | |
| 5,797,824 A | 8/1998 | Tracy | |
| 5,827,259 A | 10/1998 | Laux et al. | |
| 5,833,677 A | 11/1998 | Sauer | |
| 5,843,067 A | 12/1998 | Trombetta et al. | |
| 5,868,725 A | 2/1999 | Coles et al. | |
| 5,876,393 A | 3/1999 | Ahr et al. | |
| 5,891,125 A | 4/1999 | Plumley | |
| 5,904,672 A | 5/1999 | LeMahieu et al. | |
| 5,989,236 A | 11/1999 | Roe et al. | |
| 5,997,520 A | 12/1999 | Ahr et al. | |
| 6,022,338 A | 2/2000 | Putzer | |
| 6,142,985 A | 11/2000 | Feist | |
| 6,156,022 A | 12/2000 | Hedlund | |
| 6,180,847 B1 | 1/2001 | Ahr et al. | |
| 6,248,097 B1 | 6/2001 | Beitz et al. | |
| 6,258,076 B1 | 7/2001 | Glaug et al. | |
| 6,264,639 B1 | 7/2001 | Sauer | |
| 6,280,426 B1 | 8/2001 | Turner et al. | |
| 6,423,045 B1 | 7/2002 | Wise et al. | |
| 6,425,889 B1 | 7/2002 | Kitaoka et al. | |
| 6,458,110 B1 | 10/2002 | Lavon et al. | |
| 6,491,677 B1 | 12/2002 | Glaug et al. | |
| 6,506,185 B1 | 1/2003 | Sauer et al. | |
| 6,524,292 B1 | 2/2003 | DiPalma et al. | |
| 6,545,195 B2 | 4/2003 | Chmielewski | |
| 6,610,038 B1 | 8/2003 | DiPalma et al. | |
| 6,666,850 B1 | 12/2003 | Ahr et al. | |
| 6,685,690 B2 | 2/2004 | Ikeda et al. | |
| 6,797,858 B2 | 9/2004 | Erdman | |
| 6,881,207 B1 | 4/2005 | Tracy | |
| 7,316,674 B2 | 1/2008 | Infantino et al. | |
| 2002/0183706 A1 | 12/2002 | Valentin et al. | |
| 2003/0045848 A1 | 3/2003 | Chmielewski | |
| 2003/0050616 A1 | 3/2003 | Reynolds et al. | |
| 2003/0069555 A1 | 4/2003 | Erdman | |
| 2003/0097110 A1 | 5/2003 | Erdman | |
| 2003/0120233 A1 | 6/2003 | Ohshima et al. | |
| 2003/0120244 A1 | 6/2003 | Johnson | |
| 2004/0122393 A1 | 6/2004 | Morman et al. | |
| 2004/0147889 A1 | 7/2004 | Roe et al. | |
| 2004/0267222 A1 | 12/2004 | Erdman | |
| 2005/0148974 A1 | 7/2005 | Datta et al. | |
| 2006/0058767 A1 | 3/2006 | Zhang et al. | |
| 2006/0058768 A1 | 3/2006 | Zhang et al. | |
| 2007/0293832 A1 | 12/2007 | Wood et al. | |

FOREIGN PATENT DOCUMENTS

| | | |
|---|---|---|
| EP | 0 689 815 A1 | 1/1996 |
| EP | 0 779 065 A2 | 6/1997 |
| EP | 0 779 065 A3 | 6/1997 |
| EP | 0 802 776 B1 | 8/1999 |
| EP | 1 059 072 A2 | 12/2000 |
| EP | 1 059 072 A3 | 12/2000 |
| EP | 0 779 065 B1 | 3/2003 |
| EP | 0 802 776 B2 | 1/2005 |
| FR | 2 561 078 A1 | 9/1985 |
| WO | WO 95/00089 A1 | 1/1995 |
| WO | WO 96/21408 A2 | 7/1996 |
| WO | WO 01/15648 A1 | 3/2001 |
| WO | WO 01/21120 A1 | 3/2001 |
| WO | WO 02/083027 A2 | 10/2002 |
| WO | WO 02/083027 A3 | 10/2002 |

* cited by examiner

ABSORBENT ARTICLE WITH SEAL AND METHOD OF MANUFACTURING

RELATED APPLICATION

This application is a continuation-in-part application of U.S. patent application Ser. No. 11/423,977 filed Jun. 14, 2006 titled ABSORBENT ARTICLE WITH WAIST SEAL AND METHOD OF MANUFACTURING, which is hereby incorporated by reference in its entirety.

FIELD OF THE INVENTION

The present invention relates generally to the field of absorbent articles and, more particularly, to absorbent articles such as, e.g., diapers, with seals and methods of manufacturing the same.

BACKGROUND OF THE INVENTION

Disposable absorbent articles are used to absorb and retain body exudates, such as urine, fecal material, menses, and the like. A particular desired feature of disposable absorbent articles is the capability to acquire and hold body exudates to minimize leakage of body exudates from between the absorbent article and the wearer.

One particular problem associated absorbent articles (such as, e.g., diapers) is in the containment of low viscosity fecal matter in the rear waist region of the diaper. Leakage out the rear waist region occurs because many diapers are not able to form a seal in the small of the infant's back that is tight enough to contain, e.g., low viscosity fecal matter. This problem may be more significant for infants from zero to eight months old because infants in this age range normally have a high incidence of low viscosity fecal matter. This can also be a problem for older infants/children/adults when they are ill.

Although diapers with elastic waists have been used, that approach does not truly address the problem of sealing against the contours of the small of the back because elastic waists just bridge the generally concave contours of the small of the back. Other solutions have been proposed that involve creating an envelope along the rear waist, with an opening facing toward the crotch region of the diaper. Another approach to this problem involves adhesively sealing the diaper to the back waist region to prevent leakage. Other proposed solutions involve creating a fluid-filled pillow in the back waist region, some by elaborate mechanism to generate a gas to fill a chamber to serve as a conformable barrier in the back waist region. Examples of some of these approaches may be described in, e.g., U.S. Pat. No. 6,458,110 B1 (Lavon et al.) and International Publication No. WO 01/21120 (Reynolds et al.)

While another approach includes providing additional foam material along the back waist of the diaper in an attempt to resiliently conform to the contours of the small of the infant's back (see, e.g., U.S. Patent Application Publication No. US 2006/0058767 (Zhang et al.)), there are difficulties associated with this solution. The difficulties include the limited amount of lineal material of a thicker foam (e.g., material about 1 centimeter thick or greater) that can be delivered to the diaper manufacturing line in a conventional format, such as a roll of running length material. Providing thicker materials results in rolls having excessively large diameters or significantly shorter run times—to the point at which the use of roll-fed equipment is uneconomical.

SUMMARY OF THE INVENTION

The present invention provides absorbent articles with seals that are formed from folded stacks, discrete segments, or pleated material arranged to provide a resiliently compressible seal that can be located at one or more desired locations within the absorbent article, such as, e.g., along a central portion of the rear waist region of a diaper.

The seals are preferably constructed from relatively thin materials that (through folding, stacking, pleating, etc.) can provide a resiliently compressible seal that is thick enough and appropriately shaped to conform to the wearer's anatomy well enough to provide the desired sealing. At the same time, the continuous web material used to form the seal is preferably thin enough to be economically delivered to the manufacturing line in roll form.

In some embodiments, the seals may be provided as self-contained, discrete articles that are attached to an absorbent article during the process of assembling the absorbent article. The seals may preferably be provided in the form of resilient material located within a sealed cavity or envelope. The resilient material located within the cavity may preferably be in the form of a folded stack, pleated, stack of discrete segments, etc. as described herein. One or more openings can then be formed in the sealed cavity of the compressed seal to allow the resilient material located within the seal to expand, thereby increasing the thickness of seal from a first (compressed) thickness to a second (expanded) thickness as air enters the cavity containing the resilient material.

In one aspect, the present invention provides an absorbent article adapted to fit about the waist of a wearer, the article including a central region with absorbent material, the central region further including a first end and a second end, wherein the first end and the second end are spaced at opposite ends of the central region along a longitudinal direction; a front waist region located at the first end of the central region, wherein the front waist region extends in a lateral direction across a first end of the central region, wherein the lateral direction is generally transverse to the longitudinal direction; a rear waist region located at the second end of the central region, wherein rear waist region extends in the lateral direction across the second end of the central region; and a seal occupying a portion of the rear waist region, wherein the seal includes a folded stack of three or more layers of resilient material, wherein the folded stack has a continuous length of the resilient material with two or more folds spaced apart across the rear waist region in the lateral direction and a segment of the resilient material extending in the lateral direction between each pair of folds at opposing ends of the segment.

In another aspect, the present invention provides an absorbent article adapted to fit about the waist of a wearer, the article including a central region with absorbent material, the central region having a first end and a second end, wherein the first end and the second end are spaced at opposite ends of the central region along a longitudinal direction; a front waist region located at the first end of the central region, wherein the front waist region extends in a lateral direction across a first end of the central region, wherein the lateral direction is generally transverse to the longitudinal direction; a rear waist region located at the second end of the central region, wherein rear waist region extends in the lateral direction across the second end of the central region; and a seal occupying a portion of the rear waist region, wherein the seal includes a continuous length of resilient material gathered in a plurality of pleats, wherein the pleats include folds separating segments of the resilient material, and wherein the segments of each pleat are oriented generally transverse to a plane defined by the longitudinal and lateral directions.

In another aspect, the present invention provides an absorbent article adapted to fit about the waist of a wearer, the article including a central region with absorbent material, the central region having a first end and a second end, wherein the first end and the second end are spaced at opposite ends of the central region along a longitudinal direction; a front waist region located at the first end of the central region, wherein the front waist region extends in a lateral direction across a first end of the central region, wherein the lateral direction is generally transverse to the longitudinal direction; a rear waist region located at the second end of the central region, wherein rear waist region extends in the lateral direction across the second end of the central region; and a seal occupying an inelastic portion of the rear waist region, wherein the seal includes a stack of two or more discrete segments of resilient material, wherein the two or more discrete segments have different lengths along the lateral direction.

In another aspect, the present invention provides a method of manufacturing an absorbent article with a waist seal. The method includes folding a continuous web of resilient material to form a folded stack of three or more layers of the resilient material; separating a portion of the folded stack from the continuous web of resilient material; and attaching the folded stack of resilient material within a rear waist region of an absorbent article. The absorbent article includes a central region with absorbent material, the central region including a first end and a second end, wherein the first end and the second end are spaced at opposite ends of the central region along a longitudinal direction; and a front waist region located at the first end of the central region, wherein the front waist region extends in a lateral direction across a first end of the central region, wherein the lateral direction is generally transverse to the longitudinal direction. The rear waist region is located at the second end of the central region, wherein the rear waist region extends in the lateral direction across the second end of the central region. The folded stack of resilient material is formed from a continuous length of the resilient material with two or more folds spaced apart across the rear waist region in the lateral direction and a segment of the resilient material extending in the lateral direction between each pair of folds at opposing ends of the segment.

In another aspect, the present invention provides a method of manufacturing an absorbent article with a waist seal. The method includes pleating a continuous web of resilient material to form a pleated continuous web with plurality of pleats; separating a portion of the pleated continuous web from the continuous web to form a pleated seal; and attaching the pleated seal within a rear waist region of an absorbent article. The absorbent article includes a central region with absorbent material, the central region having a first end and a second end, wherein the first end and the second end are spaced at opposite ends of the central region along a longitudinal direction; and a front waist region located at the first end of the central region, wherein the front waist region extends in a lateral direction across a first end of the central region, wherein the lateral direction is generally transverse to the longitudinal direction. The rear waist region is located at the second end of the central region, wherein the rear waist region extends in the lateral direction across the second end of the central region. The pleated seal is formed from a continuous piece of the resilient material, wherein the pleats comprise folds separating segments of the resilient material.

In another aspect, the present invention provides a method of manufacturing an absorbent article with a waist seal. The method includes aligning two or more continuous webs of resilient material to form a continuous stacked web of two or more layers of resilient material, wherein at least two of the two or more layers comprise different widths;

separating a portion of the continuous stacked web to form a stack of discrete segments of resilient material; and attaching the stack of discrete segments of resilient material within a rear waist region of an absorbent article. The absorbent article includes a central region with absorbent material, the central region having a first end and a second end, wherein the first end and the second end are spaced at opposite ends of the central region along a longitudinal direction; and a front waist region located at the first end of the central region, wherein the front waist region extends in a lateral direction across a first end of the central region, wherein the lateral direction is generally transverse to the longitudinal direction. The rear waist region is located at the second end of the central region, wherein the rear waist region extends in the lateral direction across the second end of the central region.

In another aspect, the present invention provides a method of manufacturing an absorbent article by assembling an absorbent article that includes a central region with absorbent material, the central region having a first end and a second end, wherein the first end and the second end are spaced at opposite ends of the central region along a longitudinal direction; a front waist region located at the first end of the central region, wherein the front waist region extends in a lateral direction across a first end of the central region, wherein the lateral direction is generally transverse to the longitudinal direction; and a rear waist region located at the second end of the central region, wherein rear waist region extends in the lateral direction across the second end of the central region. The method further includes attaching a self-contained seal to the waist region during the assembling, wherein the seal includes a compressed folded stack of resilient material contained within a sealed cavity such that the compressed folded stack has a first thickness, wherein the folded stack includes a continuous length of the resilient material with two or more folds spaced apart across the rear waist region in the lateral direction and a segment of the resilient material extending in the lateral direction between each pair of folds at opposing ends of the segment; and forming an opening in the sealed cavity of the seal such that the compressed folded stack of resilient material expands to a second thickness greater than the first thickness as air enters the cavity.

In another aspect, the present invention provides a method of manufacturing an absorbent article that includes assembling an absorbent article that includes a central region with absorbent material, the central region having a first end and a second end, wherein the first end and the second end are spaced at opposite ends of the central region along a longitudinal direction; a front waist region located at the first end of the central region, wherein the front waist region extends in a lateral direction across a first end of the central region, wherein the lateral direction is generally transverse to the longitudinal direction; and a rear waist region located at the second end of the central region, wherein rear waist region extends in the lateral direction across the second end of the central region. The method further includes attaching a self-contained seal to the waist region during the assembling, wherein the seal includes resilient material gathered in a plurality of compressed pleats within a sealed cavity such that the seal has a first thickness, wherein the pleats include folds separating segments of the resilient material, and wherein the segments of each pleat are oriented generally transverse to a plane defined by the longitudinal and lateral directions; and forming an opening in the sealed cavity of the seal wherein the compressed pleats expand such that the seal has a second thickness greater than the first thickness as air enters the cavity.

In another aspect, the present invention provides a method of manufacturing an absorbent article that includes assembling an absorbent article that includes a central region with absorbent material, the central region having a first end and a second end, wherein the first end and the second end are spaced at opposite ends of the central region along a longitudinal direction; a front waist region located at the first end of the central region, wherein the front waist region extends in a lateral direction across a first end of the central region, wherein the lateral direction is generally transverse to the longitudinal direction; and a rear waist region located at the second end of the central region, wherein rear waist region extends in the lateral direction across the second end of the central region. The method further includes attaching a self-contained seal to the waist region during the assembling, wherein the seal includes a compressed stack of two or more discrete segments of resilient material contained within a sealed cavity such that the compressed stack has a first thickness, wherein the two or more discrete segments have different lengths along the lateral direction; and forming an opening in the sealed cavity of the seal such that the compressed stack of discrete segments of resilient material expands to a second thickness greater than the first thickness as air enters the cavity.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

DETAILED DESCRIPTION OF EXEMPLARY EMBODIMENTS

In the following detailed description of exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

As used herein, the term "absorbent article" refers to devices which absorb and contain body exudates, and, more specifically, refers to devices which are placed against or in proximity to the body of the wearer to absorb and contain the various exudates discharged from the body. Such absorbent articles may include, but are not limited to, diapers, training pants, incontinence briefs, diaper holders, diaper liners, and the like. The term "disposable" is used herein to describe absorbent articles that are not intended to be laundered or otherwise restored or reused as an absorbent article.

Figure 1:
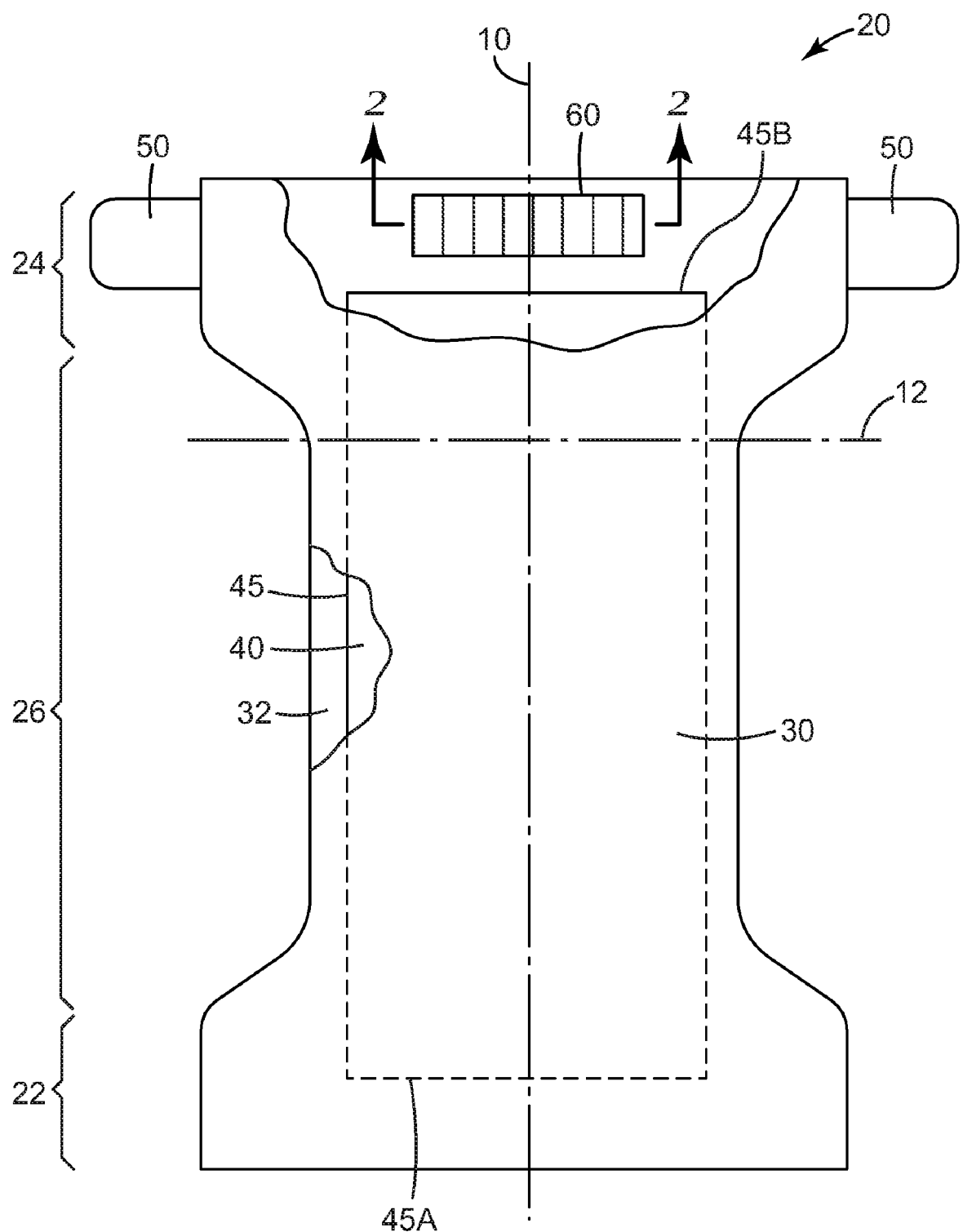
FIG. 1 is a top plan view of a disposable diaper with portions of the topsheet cutaway to illustrate other components of the diaper.

One embodiment of an absorbent article of the present invention is the unitary disposable diaper 20 shown in FIG. 1. As used herein, the term "diaper" refers to an absorbent article generally worn by infants and/or incontinent persons that is worn about the lower torso of the wearer. FIG. 1 is a plan view of the diaper 20 of the present invention in its flat-out, uncontracted state (i.e., with any elastic induced contraction pulled out). Portions of the topsheet are cutaway to more clearly show the construction of the diaper 20. The portion of the diaper 20 that faces or contacts the wearer (the body facing surface) is oriented towards the viewer in FIG. 1. The diaper 20 includes a front waist region 22, a rear waist region 24, and a central region 26. The diaper 20 also defines a longitudinal direction 10 extending between the front waist region 22 and the rear waist region 24. A lateral direction 12 is defined that is generally transverse to the longitudinal direction 10.

As used herein, the "longitudinal" direction, dimension, or axis of the diaper 20 is typically aligned front to back with respect to the wearer as the disposable absorbent article is worn (i.e., extending between the front waist region 22 and the rear waist region 24 in the view of FIG. 1). The "lateral" or "transverse" direction, dimension, or axis of the diaper 20 is generally transverse to the longitudinal direction 10 and is sideways aligned as the diaper 20 is worn. The "z-direction" for the diaper 20 is generally normal to the plane defined by the longitudinal and transverse directions 10 & 12 and can generally be considered to extend through the thickness of the diaper 20 at a selected location.

The front waist region 22 and the rear waist region 24 are those portions of the diaper 20 which, when worn, encircle the waist of the wearer and are generally the highest elevation of the diaper 20 when the wearer is in the standing position. The central region 26 is disposed between the front and rear waist regions 22, 24 and is that part of the diaper 20 which, when worn, extends between the wearer's legs.

The diaper 20 preferably includes a liquid permeable topsheet 30, a liquid impermeable backsheet 32 joined at least peripherally with the topsheet 30, and an absorbent core 40 located between the topsheet 30 and the backsheet 32. The absorbent core 40 has a perimeter 45 that includes front and rear laterally extending ends 45A and 45B. The topsheet 30, backsheet 32 and the absorbent core 40 may be assembled in a variety of well known configurations. Examples of some potentially suitable configurations are described generally in U.S. Pat. No. 3,860,003 (Buell); U.S. Pat. No. 5,151,092 (Buell); U.S. Pat. No. 6,423,045 B1 (Wise et al.); U.S. Pat. No. 6,458,110 B1 (Lavon et al.); etc.

As used herein, the term "absorbent core" refers to any component(s) of the diaper 20 used for absorbing and retaining body exudates. The absorbent core 40 may have opposed major faces and may, if desired, be encased by one or more layers of tissue. The absorbent core 40 may be made from a variety of commonly used materials such as comminuted wood pulp, typically referred to as airfelt. If desired, the absorbent core 40 may contain absorbent gelling materials as is commonly used in the art. Examples of some potentially suitable absorbent cores may be described in U.S. Pat. No. 4,610,678 (Weisman et al.); U.S. Pat. No. 4,673,402 (Weisman et al.); U.S. Pat. No. 4,834,735 (Alemany et al.); U.S. Pat. No. 5,147,345 (Young et al.); U.S. Pat. No. 5,217,445 (Cook et al.); U.S. Pat. No. 5,234,423 (Alemany et al.); etc. Absorbent gelling materials made in accordance with U.S. Pat. No. Re. 32,649 (Brandt et al.) may also be suitable for use in a diaper 20 according to the present invention.

The diaper 20 has a body facing surface formed primarily by topsheet 30 that is positioned adjacent to the wearer's body during use. The diaper 20 also has a garment facing surface that faces away from the wearer's body during use.

The diaper 20 may also preferably include a pair of fasteners 50, such as tape tabs or mechanical fasteners, positioned in the rear waist region 24 and adapted to fasten to landing areas (not shown) positioned on the garment facing surface of the front waist region 22 for fastening the diaper 20 to the wearer. Alternatively, the positions of the fasteners 50 and landing regions may be reversed. The diaper 20 may also include a variety of other features that are not depicted such as, e.g., a waist elastic feature, gasket cuffs, and barrier leg cuffs.

The absorbent articles of the present invention preferably include at least one seal 60 that may preferably be positioned, e.g., along the rear waist region 24. The seal 60 may preferably be positioned such that it is centered over the small of the back of the wearer when the absorbent article (e.g., diaper 20) is worn such that the escape of low viscosity fecal matter (and/or liquids such as, e.g., urine) between the body facing surface of the diaper 20 and the skin may be reduced. It should be understood that the location of seal 60 on the diaper 20 is only one example of a potentially suitable location for the seal. In some instances, the seal may be located lower or be wide enough such that it overlaps a portion of the absorbent core 40 (i.e., extends over or under edge 45B of absorbent core 40).

It may be preferred that the seal 60 be positioned to contact the portion of the small of the back that is occupied by the spine (sometimes referred to as the lumbar region). That region typically includes a depression aligned with the spine from which low viscosity fecal matter (and other materials) may be more likely to escape. Seals manufactured in accordance with the present invention may also be used in other areas of absorbent article where depressions in the anatomy may make their use advantageous.

It may be preferred that the seal 60 be resiliently compressible in response to compressive forces applied to the seal 60 in the z-direction (between the topsheet 30 and the backsheet 32). A resiliently compressible seal 60 may better conform to the anatomical contours of the subject wearing the diaper 20. By "resiliently compressible" as used herein, it may be preferred that the seal 60 can be compressed under a compressive force applied between the topsheet 30 and the backsheet 32 (in, e.g., the z-direction) by a compressed distance from its unrestrained thickness to a reduced thickness and that, upon release of the compressive force, expands to regain at least 50% of the compressed distance, more preferably to regain at least 75% of the compressed distance, within one (1) minute after removal of the compressive force.

Figure 2:
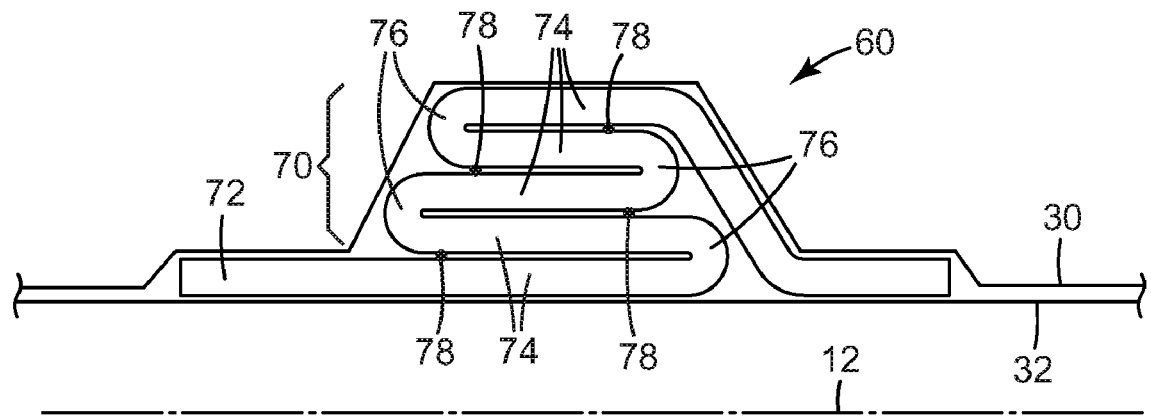
FIG. 2 is a cross-sectional sectional view of one exemplary seal in the form a folded stack taken along line 2-2 in FIG. 1.

One exemplary construction of a seal 60 is depicted in the cross-sectional view of FIG. 2 (taken along line 2-2 in FIG. 1). The seal 60 may preferably be constructed of a continuous length of material 72 that is preferably folded to form a folded stack 70. The folded stack 70 may preferably include layers of the material 72 folded such that each layer of the material 72 forms a segment 74 that that extends in the lateral direction 12 between folds 76 at opposing ends of each segment 74. The folds 76 may preferably be formed along fold lines in the material 72 that are generally aligned with the longitudinal direction 10. The material 72 of the folded stack 70 may, in some embodiments, extend across 50% or more of the rear waist region 24 (in the lateral direction 12) or the material 70 may be located only in a lesser portion of the lateral width of the rear waist region 24.

The folds 76 may preferably be formed in the material 72 without modification. In other instances, however, the folds 76 may be formed along fold lines that may include, e.g., perforations, score lines, or other modifications to make the folding easier and/or more consistent. For example, providing a row of perforations separated by land areas along each fold 76 may result in a more uniform seal shape.

It may be preferred that the folded stack 70 be located between the topsheet 30 and the backsheet 32, with the folded stack 70 located on the body facing side of the backsheet 32. Alternatively, the folded stack 70 may be located elsewhere within the thickness of the article, e.g., the folded stack 70 may be located on the body-facing surface of the topsheet 30 (with or without an additional covering over the stack 70). The backsheet 32 and/or the topsheet 30 may be attached to the folded stack 70 by any suitable technique or techniques, e.g., adhesives, ultrasonic welding, thermal welding, chemical welding, etc. It may be preferred that only one of the topsheet 30 or backsheet 32 be attached to the folded stack 70 or it may be preferred that both the topsheet 30 and the backsheet 32 be attached to the folded stack 70.

The folded stack 70 may preferably include segments 74 of material 72 with different (preferably progressively smaller) lengths such that the folds 76 within each segment 74 are closer together when moving from the back sheet 32 towards the topsheet 30. Such a convex profile (referring to the shape of the folded stack 70 as depicted in the cross-sectional view of FIG. 2) may better conform to the spinal depression in the lumbar region of a subject wearing the diaper 20. It should, however, be understood that the segments 74 in the folded stack 70 of material 72 may all have the same length between folds 76 if so desired.

It may be preferred that the folded stack 70 include three or more layers or segments 74 of the material 72. In some embodiments, the folded stack 70 may include five (or more) layers or segments 74 as depicted in FIG. 2. At an upper end, it may be preferred that the folded stack 70 include 30 or fewer layers or segments, or even 20 or fewer layers or segments.

The material 72 used to form the folded stack 70 may also be bonded to assist in retention of the folds during use. A number of bonds 78 between segments 74 are depicted in FIG. 2, although it should be understood that the depicted locations of bonds 78 are exemplary only and any suitable distribution of bonds may be used in place of the distribution depicted in FIG. 2. Furthermore, although the bonds in FIG. 2 are limited to discrete locations within the stack 70, it should be understood that the folded stack 70 may include adhesive or other bonds that occupy larger areas of the folded stack 70. Any suitable technique or techniques may be used to provide bonds in the folded stack 70 including, but are not limited to, adhesives, ultrasonic welding, thermal welding, chemical welding, etc.

If the seal 60 is to be resiliently compressible, it may be preferred that the material 72 used to construct the seal 60 be resiliently compressible as well. Examples of some potentially suitable materials that may be used to create a folded stack for use as a seal may include, but are not limited to, foam material, nonwovens (such as, e.g., lofted nonwoven materials used in, e.g., batting), etc.

In some instances, the material 72 of the folded stack 70 may also be elastic, i.e., the material 72 may exhibit elasticity when stretched along its length and/or over its width. As used herein, the term "elasticity" (and variations thereof) means that the article in question (e.g., the material 72) will substantially resume a significant portion of its original shape after being stretched. It may be preferred that the recovery of an elastic portion be at least 20% of the elongation experienced as a result of moderate stretching (e.g., undergoing elongation of about 150% of original length).

If the material 72 of the folded stack 70 is elastic and the rear waist region 24 of the diaper 20 is also elastic, it may be preferred to include a stabilizing layer within the portion of the rear waist region 24 occupied by the folded stack 70 to limit deformation of the folded stack 70 if the rear waist region 24 is elastically stretched during use (examples of potentially suitable stabilizing layers are described in connection with other exemplary embodiments of seals herein). Such a stabilizing layer may be inelastic or elastic as desired.

Figure 3:
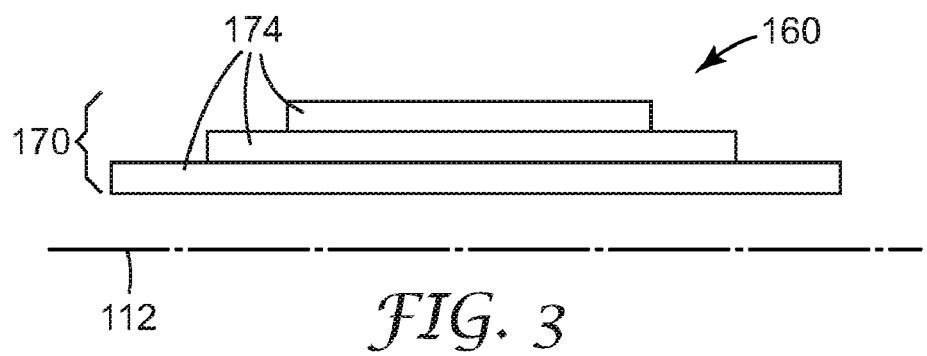
FIG. 3 is a side elevational view of another exemplary seal in the form of a stack of discrete segments of resiliently compressible material.
Figure 4:
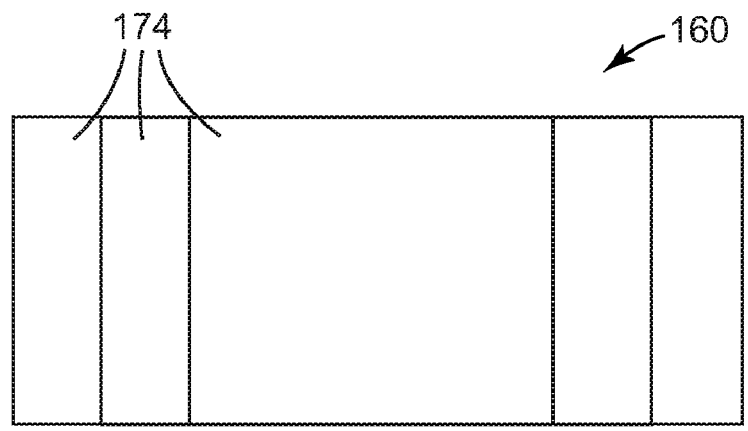
FIG. 4 is plan view of the seal of FIG. 3.

An alternative embodiment of a seal 160 that may be used in connection with the present invention is depicted in FIGS. 3 & 4. The seal 160 may be in the form of a stack 170 of two or more discrete segments 174 of material arranged and attached to each other to form a resiliently compressible seal 160 that may be located between the topsheet and backsheet of a diaper (not shown). Discrete segments 174 are segments of the resilient material that are not connected to each other along their ends. For example, the discrete segments 174 may be supplied by separate rolls, slit from a single roll, or provided from a stack, etc.

The segments 174 may preferably be bonded to each other as discussed above in connection with the folded stack to maintain a selected arrangement between the different segments. Further, it may be preferred that the segments 174 within the stack 170 have different lengths along the lateral direction 112 and those segments 174 may preferably be arranged to provide a seal 160 with a generally convex profile (as seen in FIG. 3) that may better conform to the depression formed proximate the spine within the lumbar region of a wearer.

The materials used to form the stack 170 may preferably be similar to those used in connection with the folded stack discussed herein. In one variation, however, in a stack 170 formed from discrete segments 174, the materials used in the segments 174 may be the same or different. For example, the materials used in different segments may have different properties such as, e.g., compressibility, firmness, elasticity, etc. It may be preferred, for example, to use softer, more easily compressed materials proximate the topsheet (the body facing side of the stack 170) and firmer materials towards the backsheet side of the stack 170. Such an arrangement may provide improved conformability to the seal 160.

Figure 5:
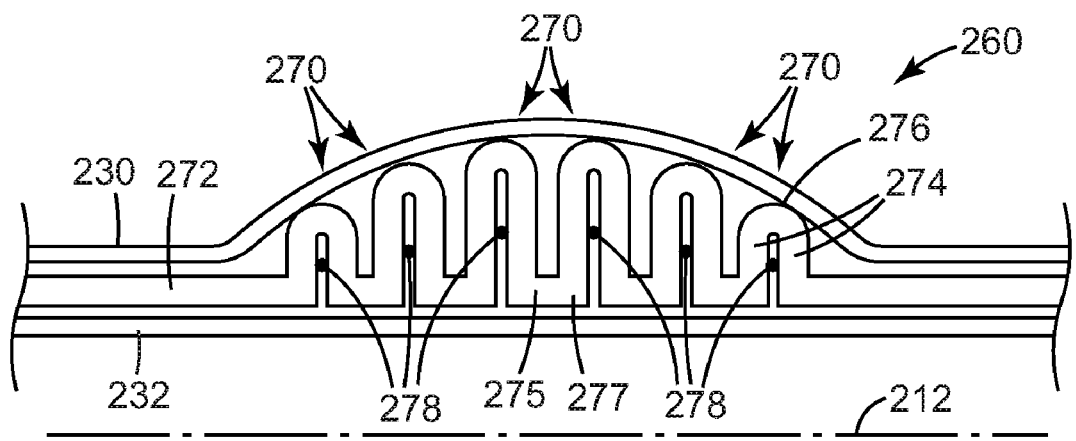
FIG. 5 is a cross-sectional view of another exemplary seal including pleats of a resilient material.

Another exemplary embodiment of a seal 260 that may be used in connection with the present invention is depicted in the cross-sectional view of FIG. 5. The seal 260 includes pleats 270 formed of upright segments 274 of a web material 272 using folds 276 & 277 to define the upright segments 274. Each pleat 270 preferably includes two upright segments 274 with peak fold 276 connecting the two segments 274. The opposite ends of the upright segments 274 (the ends nearest backsheet 232) include base folds 277.

The material 272 used to form the pleats 270 may preferably be similar to that used in connection with the folded stack discussed herein. Further, the pleats 270 (and connecting segments 275, if provided) may be formed from a continuous length of the material used to form the pleats 270. That material may extend, in some embodiments, across 50% or more of the width of the rear waist region in the lateral direction 212 or it may be located within only the portion of the lateral width of the rear waist region in which the seal 260 is located.

The upright segments 274 may preferably be oriented generally transverse to a plane that is defined by the longitudinal direction (not shown in FIG. 5) and the lateral direction 212. Such a plane may be considered as coinciding with the backsheet 232 in the embodiment of FIG. 5. As a result, the upright segments 274 and the pleats 270 they form may preferably extend from the backsheet 232 towards the body of a subject wearing the disposable article in which seal 260 is provided (although the opposite orientation may also be used—with the pleats 270 extending from the topsheet 230 away from the body of a subject wearing the disposable article).

In the depicted embodiment, adjacent pleats 270 may preferably be separated from each other in the lateral direction 212 (e.g., across the rear waist region of a diaper) as depicted in FIG. 5, such that adjacent pleats 270 preferably do not contact each other (when the seal 260 is uncompressed). The adjacent pleats 270 are separated from each other between base folds 277 by a lateral segment 275 that extends in the lateral direction 212. Alternatively, the pleats in a seal according to the present invention could be located immediately adjacent each other (in the lateral direction 212). In such a case, it may be preferred that the base fold located between the adjacent pleats be shared, i.e., the base fold may define adjacent segments in the adjacent pleats with no lateral segment 275 being provided between the adjacent pleats.

The segments 274 in each of the pleats 270 may preferably include one or more bonds 278 that connect the segments 274 within the pleat 270. The bonds 278 may assist in retaining the shape of the pleats 270 (and, therefore, the seal 260) in response to compression between the topsheet 230 and the backsheet 232. Any suitable technique or techniques may be used to provide bonds 278 between the segments 274 in the pleats 270 including, but not limited to, adhesives, ultrasonic welding, thermal welding, chemical welding, etc. Although only one bond 278 is depicted in connection with each pleat 270, it should be understood that two or more bonds may be provided or that some pleats may include one or more bonds while others do not include bonds. Further, the bonds 278 may be provided in limited areas (e.g., at points or along lines) as depicted in FIG. 5 or, alternatively, the segments 274 within a pleat 270 may be bonded together over more significant portions of their common surfaces (i.e., the surfaces of segments 274 that face each other within the pleat 270).

Although not depicted, the pleats 270 may also be bonded or attached to the topsheet 230 and/or the backsheet 232. Such bonds may also assist in retaining the overall shape of the pleats 270 and, therefore, the seal 260.

The seal 260 may preferably include pleats 270 that include segments 274 with different lengths such that the peak folds 276 are located at different distances from the base folds 277. It may be preferred that the pleat height (the distance between peak fold 276 and the base folds within a pleat 270) reach a maximum proximate a lateral center of the seal 260 as depicted in FIG. 5 with the pleats 270 on each side of the lateral center having a decreasing pleat height. Such an arrangement may preferably provide a seal 260 having a generally convex profile (referring to the general shape of the seal 260 as depicted in FIG. 5). A seal 260 with a convex profile may better conform to the spinal depression in the lumbar region of a subject wearing the article including the seal 260. It should, however, be understood that the pleats 270 in a seal 260 may all have the same pleat height or may have any other selected arrangement (e.g., concave, sinusoidal, etc.) if so desired.

Figure 6:
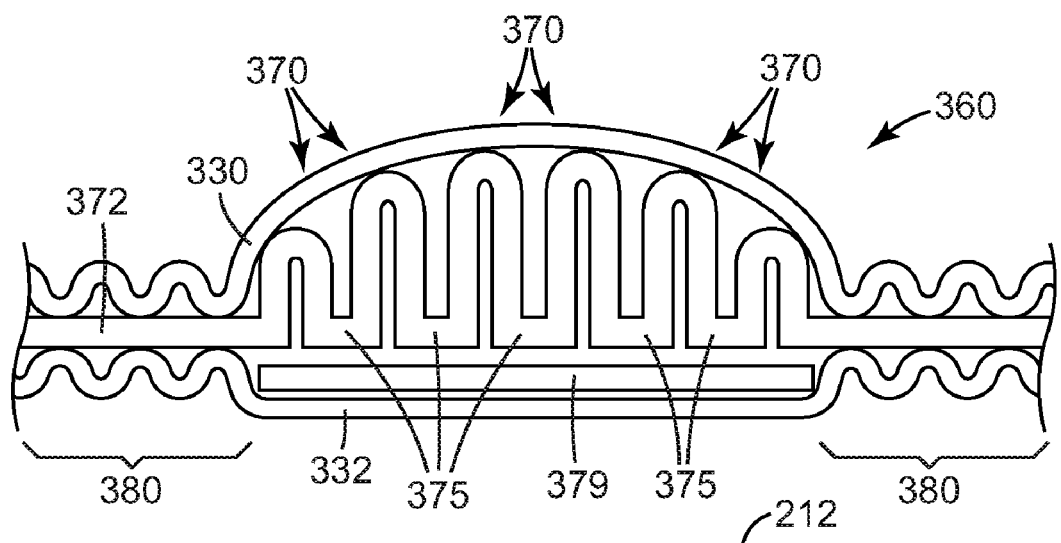
FIG. 6 is a cross-sectional view of another exemplary seal including pleats of an elastic resilient material.

Still another exemplary embodiment of a seal 360 is depicted in the cross-sectional view of FIG. 6. In many respects, the seal 360, which includes pleats 370 arranged in a manner similar to those found in seal 260 of FIG. 5, may be constructed in a manner similar to seal 260.

One optional difference in pleated seal 360 as compared to pleated seal 260 is that the material used to construct the pleats 370 may be elastic such that the connecting lateral segments 375 between pleats 370 may also exhibit elasticity. In instances where it may be desirable that the material of the pleats 370 exhibit elasticity, but that the segments 375 connecting the bases of the pleats 370 do not exhibit elasticity, a stabilizing layer 379 may be provided proximate the bases of the pleats 370 to inhibit stretching of the seal 360 in the lateral direction 312 during use of the seal 360.

In some instances, the stabilizing layer 379 may be inelastic, such that the portion of the waist region connected to the stabilizing layer 379 is inelastic. In other instances, the stabilizing layer 379 may itself be elastic, with the stabilizing layer 379 merely adding resistance to stretch within the portion of the waist region connected to the stabilizing layer 379. The stabilizing layer 379 may be constructed of any suitable material or materials, e.g., nonwoven webs, filaments, multi-component webs, films, etc. In some instances, the stabilizing layer 379 may be constructed of the same material used to form pleats 370 and/or interconnecting segments 375.

The stabilizing layer 379 may be bonded to any selected component(s) within the seal 360 or the absorbent article incorporating the seal 360, e.g., the pleats 370, connecting segments 375, topsheet 330, backsheet 332, etc. Any suitable technique or techniques may be used to provide the bonds, including, but not limited to, adhesives, ultrasonic welding, thermal welding, chemical welding, etc.

Where the material 372 used to form pleats 370 is elastic, the elasticity of the material 372 may be advantageously used to provide elasticity to the surrounding portions of the waist region. As seen in FIG. 6, the seal 360 is surrounded on each side by elastic waist portions 380. It may be preferred that portions of the article including seal 360 include components that may be gathered on the elastic material 372 as depicted in FIG. 6. Such gathering may be accomplished by. e.g., attaching the topsheet 330 and the backsheet 332 to the elastic material 372 while the material 372 is stretched. When the material 372 is released, it draws or gathers the attached components in manners that are well known to those skilled in the art.

While a variety of embodiments of seals according to the present invention have been described herein, other potential advantages of the present invention may be found in methods of manufacturing absorbent articles incorporating the resiliently compressible seals. Such manufacturing processes are typically web-based, that is they rely on the use of webs of different materials unwound from rolls that are processed by folding, sheeting, cutting, slitting, etc. to form a desired absorbent article. In place of roll-fed assembly processes, one or more of the webs may be manufactured in line with the assembly process to potentially provide additional manufacturing advantages.

As discussed herein, a potential advantage of the seals of the present invention is their use of relatively thin webs of material that is folded into a stack, provided in discrete segments that are stacked, or formed into pleats to provide a seal with a desired thickness and resilient compressibility that cannot be provided by a single layer of the relatively thin material alone.

Figure 7:
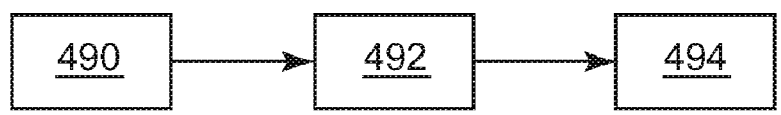
FIG. 7 is a block diagram of one system/method of manufacturing a waist seal according to the present invention.

FIG. 7 depicts a system and method in which seal material 490, which may preferably be provided in roll form or manufactured in-line with the seal assembly process, is directed into seal forming equipment 492. The seal forming equipment 492 is preferably capable of accepting the seal material 490 in the form of a continuous web, as individual sheets (which may be fed from a continuous roll or stack), etc. Depending on the construction of the seal to be used, the seal forming equipment may convert (e.g., fold, sheet, cut, stack, pleat, etc.) the seal material 490 as needed to construct a seal which is applied to an absorbent article by an applicator 494. In some instances, the converting and application may be completed at the same station.

The equipment used to convert the material in the seals of the present invention may be selected based on the properties of the materials, speed of the manufacturing process, etc. Examples of some potentially suitable converting equipment may be found in, e.g., U.S. Pat. No. 4,421,501 (Scheffer); U.S. Pat. No. 4,488,927 (Hooper); U.S. Pat. No. 4,614,512 (Capdeboscq); U.S. Pat. No. 4,682,977 (Buxton); U.S. Pat. No. 5,007,890 (Alverth et al.); U.S. Pat. No. 5,300,007 (Kober); U.S. Pat. No. 5,556,360 (Kober et al.), etc. If included in the seals, the seal forming equipment may include bonding apparatus (e.g., adhesive applicators, welding equipment, etc.), perforating apparatus, etc. as required to form the seals.

Figure 8:
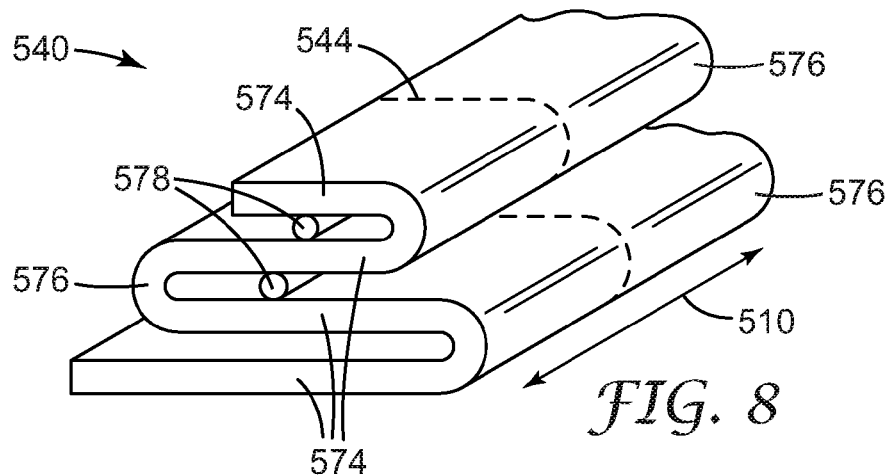
FIG. 8 depicts a portion of one continuous web of resilient material folded for use as a waist seal.

FIG. 8 depicts a portion of one continuous web 540 of resilient material that is folded for use as a waist seal. It may be preferred that the folding be along fold lines 576 that extend along the length 510 of the continuous web 540. After folding, it may be preferred that the web 540 be separated (e.g., sheeted) along lines 544 that extend across the width of the web 540 (where the width is generally transverse to the length 510).

Also depicted in FIG. 8 are bonds 578 between the segments 574 of the folded stack. It may be preferred that the bonds 578 (which may be formed by, e.g., applying adhesive, welding, etc.) attach the segments 574 at selected locations along the length 510 of the continuous web 540.

Figure 9:
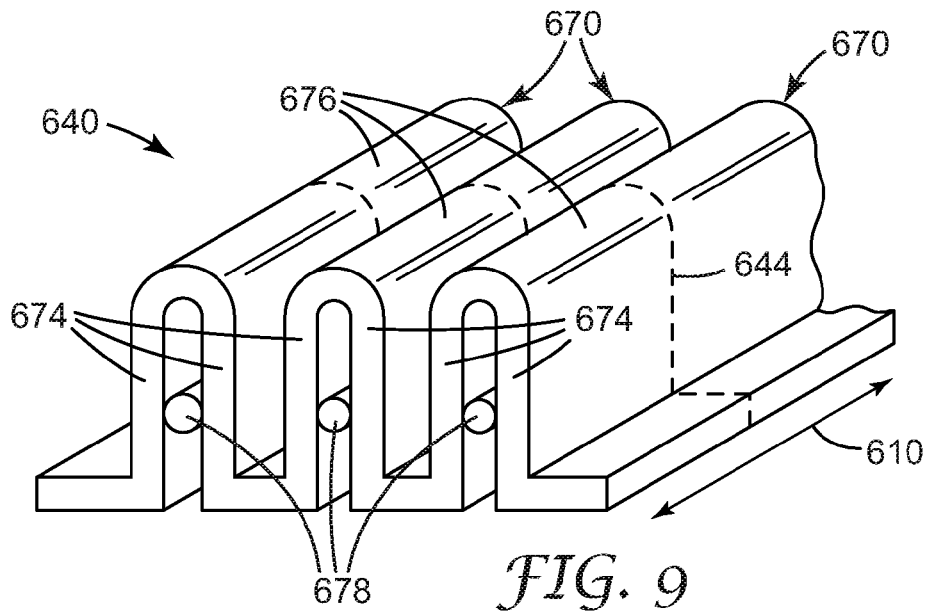
FIG. 9 depicts a portion of another continuous web of resilient material that is pleated to form a pleated seal according to the present invention.

FIG. 9 depicts a portion of another continuous web 640 of resilient material that is pleated to include pleats 670 in a pleated seal according to the present invention. It may be preferred that the pleating be along fold lines 676 that extend along the length 610 of the continuous web 640. After the pleats 670 have been formed, it may be preferred that the pleated web 640 be separated (e.g., sheeted) along lines 644 that extend across the width of the web 640 (where the width is generally transverse to the length 610).

Also depicted in FIG. 9 are bonds 678 between the segments 674 of the pleats 670. It may be preferred that the bonds 678 (which may be formed by, e.g., applying adhesive, welding, etc.) attach the segments 674 at selected locations along the length 610 of the continuous web 640.

Figure 10:
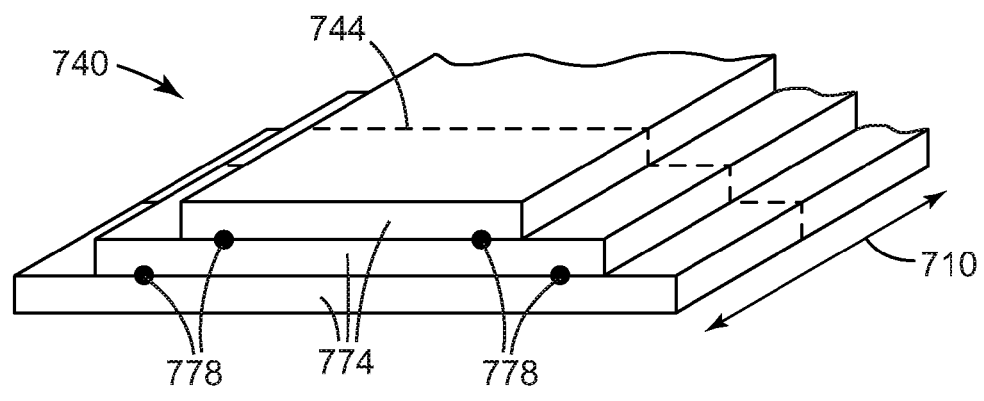
FIG. 10 depicts a portion of another continuous web that includes a plurality of layers stacked to form a seal in the form of a stack of discrete segments according to the present invention.

FIG. 10 depicts a portion of another continuous web 740 of resilient material that includes a plurality of layers 774 stacked to form a seal including a stack of discrete segments according to the present invention. It may be preferred that the stacking be accomplished by aligning separate continuous webs for each layer 774 using, e.g., separate rolls of resilient material that are unrolled and aligned as desired. Alternatively, two or more layers 774 of the stack may be provided by slitting a single wider web into narrower webs that can be realigned to form a stacked arrangement as depicted in FIG. 10. At least two of the different webs and their resulting layers 774 may preferably have different widths (where width is measured generally transverse to length). In some embodiments, all of the layers 774 within the continuous web 740 may be constructed of the same material. In other embodiments, at least two layers 774 within the continuous web 740 may be constructed of different materials.

Each layer 774 preferably extends along the length 710 of the stacked continuous web 740. After the stacked continuous web 740 has been formed, it may be preferred that the web 740 be separated (e.g., sheeted) along lines 744 that extend across the width of the stacked web 740 (where the width is generally transverse to the length 710).

Also depicted in FIG. 10 are bonds 778 between the layers 774 of the stacked web 740. It may be preferred that the bonds 778 (which may be formed by, e.g., applying adhesive, welding, etc.) attach the segments 774 at selected locations along the length 710 of the stacked web 740.

Although the resiliently compressible seals have been described herein as preferably having a generally convex profile taken in a z-direction plane that is transverse to a plane formed by the lateral and longitudinal directions and parallel to the lateral direction (see, e.g., the cross-sectional or side views of FIGS. 2, 3, 5, and 6), seals having alternative profiles are also possible. For example, the seals manufactured according to the present invention may have a generally rectangular cross-section profile in such a z-direction plane.

Figure 11:
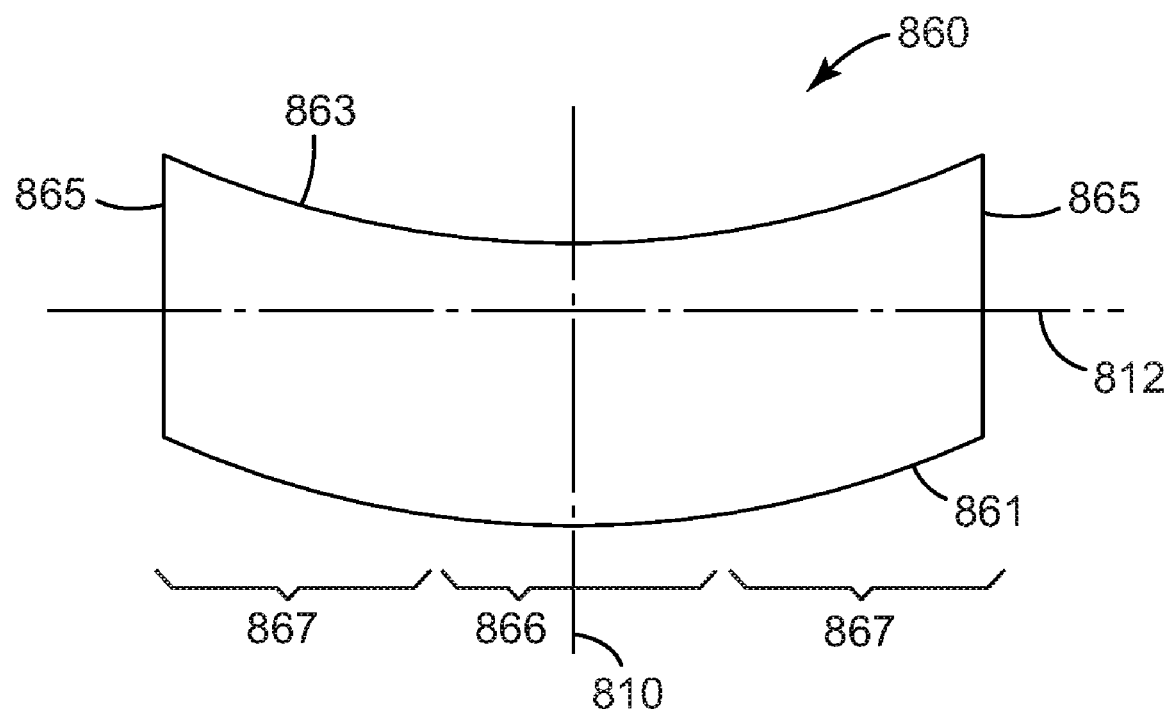
FIG. 11 depicts an alternative shape for a seal in the plane defined by the longitudinal and lateral directions.

In yet another alternative, although the seals depicted in the figures may have a rectangular shape in the plane defined by the lateral and longitudinal directions (e.g., the plane occupied by the paper on which FIG. 1 is printed), seals of the present invention may have other shapes. One such alternative shape is depicted in FIG. 11, in which the seal 860 has a lower edge 861, upper edge 863 and sides 865. Both the longitudinal direction 810 and lateral direction 812 are also depicted in FIG. 11 (with the longitudinal direction 810 and the lateral direction 812 defining the plane in which the shape of the seal 860 is defined).

It may be preferred that the lower edge 861 be shaped to divert the flow direction of low viscosity materials traveling in the longitudinal direction. The lower edge may preferably divert that flow at least partially along the lateral direction 812. Flow diversion may be accomplished using any seal with a lower edge that is not aligned with the lateral direction 812 that extends across the waist region of the absorbent article (as would the lower edge of a rectangular seal aligned arranged as depicted in, e.g., FIG. 1).

In some embodiments, it may be preferred that the seal have a lower edge 861 that is not aligned with the lateral direction 812 and that exhibits symmetry about a centerline aligned with the longitudinal direction 810. One such embodiment is depicted in FIG. 11 where the seal 860 includes an intermediate section 866 flanked on both sides by outer sections 867. It may be preferred that the intermediate section of the lower edge of seal 860 be located closer to the central region of an absorbent article (not shown in FIG. 11) in which the seal 860 is used. Although one such shape for the lower edge 861 is a convex curve as depicted in FIG. 11, many other shapes are possible, e.g., V-shapes, etc. Low viscosity materials flowing towards the lower edge 861 along the longitudinal direction 810 may preferably be diverted to flow along the edge 861 towards the outer sections 867.

Also seen in FIG. 11 is that the upper edge 863 of the seal 860 may preferably have a shape that is complementary to the shape of the lower edge 861. In the depicted seal, lower edge 861 is convex while upper edge 863 is concave. One potential advantage of such an arrangement is that as seals 860 are, e.g., sheeted from web that extends in the longitudinal direction 810, little or no material is wasted because the upper edge 863 defines the lower edge of the next seal in the web. It should be noted that the longitudinal symmetry of the seal 860 also contributes to the reduced waste along with complementary lower and upper edges 861 and 863.

The seals used in connection with the present invention may also be characterized on the basis of the dimensions of the seals and/or the materials used to form the seals. For example, it may be preferred that the resilient material used in the stacks, pleats, etc. have a thickness of 1 millimeter (mm) or more, preferably 1.5 mm or more. It may be preferred that the upper end of the thickness of the resilient material be 4 mm or less, or even 2.5 mm or less.

The maximum thickness of the seals (in the z-direction) may preferably be 4 mm or more, or even 6 mm or more. At the upper end, it may be preferred that the thickness of the seal be 15 mm or less, or even 10 mm or less.

For folded or stacked seals as discussed herein, it may be preferred that the width of the seal at the base along the lateral direction (i.e., across the rear waist region) be 25 mm or more, or even 30 mm or more. At the upper end of the range, it may be preferred that base of the seal have a lateral direction width of 60 mm or less, or even 45 mm or less. At the top of a folded or stacked seal. it may be preferred that the top-most layer have a lateral direction width of 5 mm or more, or even 10 mm or more. At the upper end of that range, it may be preferred that the top-most layer have a lateral direction width of 35 mm or less, or even 25 mm or less.

In the longitudinal direction along, it may be preferred that the length of the seal be 15 mm or more, or even 20 mm or more. At the upper end of the range, it may be preferred that the longitudinal length of the seals be 50 mm or less, or even 40 mm or less.

The entire lateral direction width of the resilient material incorporated into the absorbent article (i.e., that portion extending laterally from the stacked/pleated portion) may, in some embodiments, preferably be 75 mm or more. At the upper end of that range, it may be preferred that the entire lateral direction width of the resilient material incorporated into the absorbent article (i.e., that portion extending laterally from the stacked/pleated portion) be 150 mm or less.

The seals used in connection with absorbent articles of the present invention may, in some instances, be provided as self-contained, discrete articles that are attached to an absorbent article during the process of assembling the absorbent article. The seals may preferably be provided in the form of resilient material located within a cavity or envelope. The resilient material located within the cavity may preferably be in the form of a folded stack, pleated, stack of discrete segments, etc. as described herein.

Figure 12:
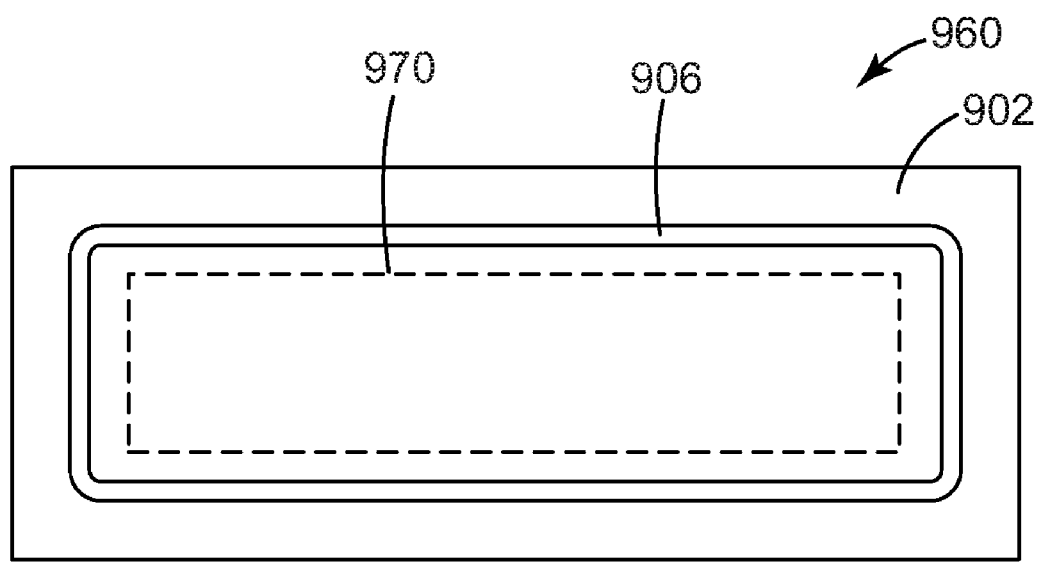
FIG. 12 is a plan view of one exemplary embodiment of a self-contained, compressed seal for use in an absorbent article according to the present invention.
Figure 13:
FIG. 13 is an edge view of the self-contained compressed seal of FIG. 12 while the seal is in a compressed state.
Figure 14:
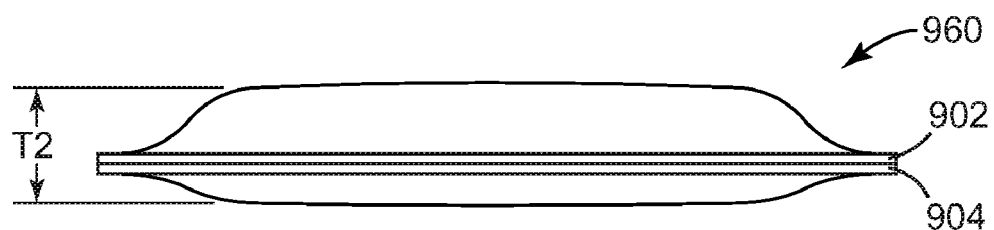
FIG. 14 is an edge view of the self-contained compressed seal of FIG. 12 with the seal is in an expanded state.

One example of a self-contained seal that may be used in connection with the present invention is depicted in FIGS. 12-14. The seal 960 preferably includes resilient material 970 located between layers 902 and 904. The layers 902 and 904 are preferably joined together along bonded seal 906 to form a sealed cavity within which the resilient material 970 is located. The bonded seal 906 between layers 902 and 904 can be formed by any suitable technique or techniques, such as heat/pressure sealing, adhesive bonding, ultrasonic bonding, etc.

The two layers 902 and 904 used to form the sealed cavity may be the same material or different materials (provided the different materials can be bonded to each other to form the desired sealed cavity). The two layers 902 and 904 can be formed from two separate pieces of material. Alternatively, the two layers 902 and 904 of material can be formed from a single piece of material that is folded along one edge to form the sealed cavity. In another alternative, the sealed cavity can be formed from a tube in which the ends are bonded together with the resilient material located therein.

The self-contained seal 960 is depicted in a compressed state in the edge view of FIG. 13 and in an expanded state in FIG. 14. As discussed herein, the resilient material 970 located within the seal 960 may preferably be compressed when sealed within the cavity formed between layers 902 and 904 such that the bonded seal 960 exhibits a reduced thickness (T1 in FIG. 13) until one or more openings are formed in the sealed cavity to allow air (or any other suitable fluid) to enter the sealed cavity. After the one or more openings are formed, the resilient material 970 located within the seal 960 expands to a second thickness (T2 in FIG. 14) as air enters the cavity containing the resilient material 970. As depicted in FIGS. 13 & 14, the second, expanded thickness T2 is larger than the compressed thickness T1.

If, for example, the resilient material is provided in the form of a compressed folded stack of resilient material (see, e.g., FIG. 2) having a z-axis thickness of T1, then the compressed folded stack of resilient material expands to a second thickness T2 that is greater than the first thickness as air enters the cavity.

If the seal includes resilient material gathered in a plurality of compressed pleats within a sealed cavity having a z-axis thickness of T1, then the compressed pleats expand after forming the one or more openings such that the seal has a second thickness T2 that is greater than the first thickness as air enters the cavity. As used in connection with the present invention, "compressed pleats" would typically be deformed from the shape they take when the seal is expanded.

If, in another alternative, the seal includes a compressed stack of two or more discrete segments of resilient material contained within a sealed cavity, then the compressed stack of discrete segments of resilient material expands from a first compressed thickness T1 to a second expanded thickness T2 that is greater than the first thickness as air enters the cavity.

The compressed resilient material 970 of seal 960 does not expand within sealed cavity before the one or more openings are formed therein because the interior of the cavity is in pressure equilibrium with the ambient atmosphere. As such, expansion would increase the volume within sealed cavity, which would lower the air pressure within sealed cavity. Accordingly, the atmospheric pressure outside the sealed cavity 960 operates to limit expansion of compressed resilient material 970 within the sealed cavity.

The term "compressed" as applied to seal 960 has a reduced thickness (T1), by virtue of the application thereto of a compressive force, as compared to its expanded thickness (T2). The reduced thickness (T1) of seal 960 may preferably be no more than about one half the expanded thickness of seal 960 as depicted in FIGS. 13 & 14.

The materials used to construct the sealed cavity are preferably impermeable to air such that if the resilient material is compressed while the cavity is sealed, air is prevented from entering the cavity. As a result, the resilient material within the sealed cavity will remain compressed until an opening is formed that will allow air to enter the cavity. Upon the entry of air into the cavity, the resilient material will preferably expand such that the seal becomes "resiliently compressible" as described herein. It may be preferred that the seal be delivered to the absorbent article assembly process in the compressed state and expanded after attachment to the absorbent article. In other instances, the seal may be delivered to the absorbent article assembly process in the compressed state and expanded before attachment to the absorbent article.

Suitable materials for constructing a cavity for a self-contained seal are preferably impermeable to air. As discussed herein, materials will be considered as impermeable to air if they are capable of preventing the transmission of air to such an extent that the resilient material located within the seal remains compressed until an opening is formed to allow air into the cavity. For example, suitable impermeable materials may preferably resist air infiltration into the salad cavity such that the resilient material retains a desired degree of compression for a period of at least one day (preferably for a period of at least one week) when stored under atmospheric pressure at a temperature of 20 degrees Celsius and 50% relative humidity.

The materials used to form the sealed cavity may also preferably be amenable to the controlled formation of one or more opening in the sealed cavity to allow air to enter and expand the resilient material located therein. In other words, the materials used for the sealed cavity will preferably resist bursting or fracturing as an opening is formed therein to allow the entry of air into the sealed cavity at a selected time. Useful materials may include, e.g., polymeric films that can be bonded to each other by conventional bonding methods such as, e.g., heat sealing, ultrasonic bonding, adhesive bonding, etc.

In addition to air impermeability, the materials used in the layers forming the sealed cavity are preferably flexible such that they can accommodate expansion of the resilient material after one or more openings are formed in the sealed cavity. It may be preferred that the materials also be extensible such that they can stretch to accommodate the expansion. In one embodiment of the present invention one or both of the layers can be formed from an elastomeric or stretchable film. Alternatively, one or both of the layers can be pre-formed, such as by vacuum forming or embossing, to accommodate expansion of resilient element. In another alternative, one or both of the layers can be folded, pleated, etc., so as to accommodate expansion of the resilient element. That is, the outer layers can be inextensible and accommodate expansion of the resilient member simply by changing to a higher volume shape, such as an arced, circular, rectangular, or other shape.

The resilient material located within the sealed cavity is preferably made of resiliently compressible material such that when the seal is in a compressed state and one or more openings are formed in the sealed cavity, the entry of air allows the resilient material to expand to an increased thickness. In one embodiment, the resilient material can be in the form of a porous, sponge-like structure such as an open-celled foam (e.g., a polymeric foam). In an alternative to foams, other resiliently compressible materials may be used, e.g., nonwovens, etc.

The resiliently compressible materials used in the seals of the present invention may preferably be provided from relatively thin materials that (through folding, stacking, pleating, etc.) can provide a resiliently compressible seal that is thick enough and appropriately shaped to conform to a wearer's anatomy as discussed herein.

The self-contained compressed seals of the present invention may be formed by a variety of methods such as, e.g., placing resilient material in between layers of impermeable material and compressing the resilient material while joining and sealing the layers together around the resilient material to form a sealed cavity in which the compressed resilient material is located. Rather than relying only on physical compression to remove air from the resilient material compressed between the impermeable layers, a mechanical system (e.g. a vacuum pump) can be use to more completely remove air from the seal while forming the sealed cavity.

Referring again to FIG. 12, although the resilient material 970 is depicted as being located within the boundaries of the bonded seal 906 that defines the sealed cavity of seal 960, in some embodiments the resilient material may extend into the bonded seal 906. Because, however, the bonded seal 906 is preferably air impermeable, the resilient material is preferably capable of processing (e.g., can be densified or collapsed) within the bonded seal 906 such that the bonded seal is air impermeable. This may allow flexibility in that continuous web-based manufacturing processes can be used rather than piecewise handling of resilient material. Such a manufacturing process could be carried out if, for example, the impermeable layers 902 and 904 are a material such as a thermoplastic polyolefin and the resilient material 970 is an expanded thermoplastic polyolefin. In such an embodiment, the bonded seal 906 may be formed by heat sealing such that the resilient material 970 collapses and becomes melt bonded to the films of layers 902 and 904 so as to form an air-impermeable bond.

Figure 15:
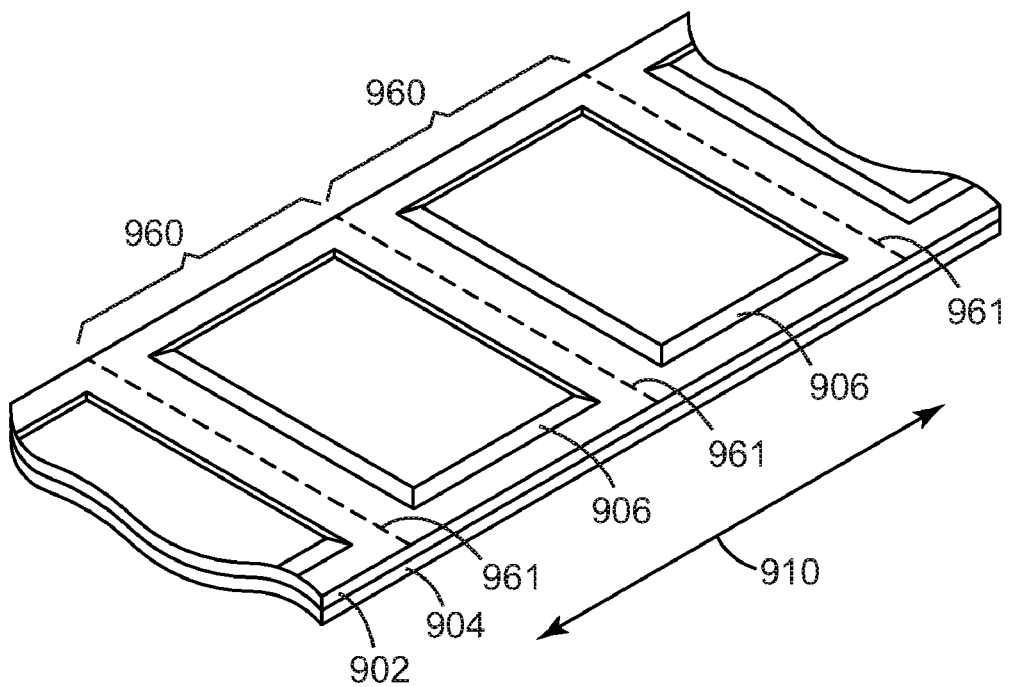
FIG. 15 is a perspective view of a portion of a web that includes multiple self-contained, compressed seals connected along a length of the web.

The self-contained seals of the present invention may be supplied in the assembly or manufacturing process of an absorbent article in a variety of forms. For example, the seals may be supplied as individual piece parts that are handled and placed in a selected location individually. Seal 960 depicted in FIG. 12 is an example of one such individual self-contained seal. Alternatively, the seals may be supplied in a continuous web of connected seals. FIG. 15 depicts one example of such an embodiment in which the multiple seals 960 are connected such that they form a web extending along a length 910. Each of the seals 960 is preferably a self-contained, compressed seal in accordance with the principles of the present invention. The seals 960 may preferably be separated from the web along lines 961 in FIG. 15 by, e.g., cutting, tearing, etc. When delivered in web form, it may be preferred that seals 960 remain compressed to reduce the size of the rolls containing the webs.

Methods of assembling or manufacturing absorbent articles (such as, e.g., diapers) that include self-contained seals of the present invention may involve attachment of the sealing member at a selected location during any part of the assembly process. For example, the self-contained seal may be attached at a selected location before the individual absorbent articles have been separated (e.g., sheeted) from a web or, alternatively, the self-contained seals may be attached to the absorbent article at a selected location at the same time or after the absorbent article has been separated from a web.

If the self-contained seals are attached at the beginning or at some intermediate step in the assembly process of the absorbent articles, they may be attached to the top sheet, bottom sheet, or some other component of the absorbent article. It may be preferred that the self-contained seals be attached within a waist region of the absorbent article, regardless of which component the seal is attached to or at what point in the assembly process the seal is attached.

Another variable when attaching a compressed self-contained seal to an absorbent article during the process of assembling the absorbent article is selecting when to form one or more openings in the sealed cavity to allow the compressed seal to expand. The one or more openings may be formed after the absorbent article is partially or completely assembled. That is, the one or more openings may be formed before or after any or all of the other absorbent article components (elastics, side panels, fastening systems, etc.) are assembled to form the finished absorbent article product. In addition, the one or more openings may be formed before attaching the seal to the absorbent article, after attaching the seal to the absorbent article, or while attaching the seal to the absorbent article.

If the self-contained seals are provided in a continuous web form in which multiple seals are connected as described herein, another option is when to separate the self-contained seals from the web. The seals may be separated from the web before attaching the seals to the absorbent article, after attaching the seals to the absorbent article, or while attaching the seals to the absorbent article.

As discussed herein, the self-contained seals used in connection with the present invention may preferably be compressed such that resilient material is contained within an air-impermeable sealed cavity in a compressed state until one or more openings are formed in the sealed cavity to allow air to enter. As air enters, the resilient material expands—thus expanding the seal. The one or more openings in the sealed cavity may be formed by any suitable technique or techniques. Examples of some potentially suitable techniques and/or structures for providing openings in sealed cavities may be described in, e.g., U.S. Pat. No. 5,520,674 (Lavon et al.); U.S. Pat. No. 6,423,045 (Wise et al.); and U.S. Pat. No. 6,458,110 (Lavon et al.). Briefly, however, the openings may be formed by piercing, slitting, tearing, removing a cover from an opening, etc. The openings may be formed using, e.g., needles, blades, punch dies, laser energy, etc. If the self-contained seals are provided in a continuous web form as described herein, the one or more openings may also be formed as a part of the process of separating the individual seals from the web.

The size of the opening or openings formed in the sealed cavity may be selected to allow for controlled expansion of the resilient material located within the seal. If the seals are to be compressed after expanding to, for example, package the absorbent articles after they have been manufactured, the size of the one or more openings may also be selected to allow for a compression rate that is fast enough given the constraints of the packaging process.

If multiple openings are formed, they may be formed at different times or all of the openings may be formed at the same time. Multiple openings may be spaced relatively close together or they may be distributed over the seal in a selected pattern.

If the self-contained seals are provided in a continuous web form as described herein, the one or more openings may also be formed as a part of the process of separating the individual seals from the web.

The complete disclosure of the patents, patent documents, and publications cited herein are incorporated by reference in their entirety as if each were individually incorporated.

Exemplary embodiments of this invention are discussed and reference has been made to possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention claimed is:

1. A method of manufacturing an absorbent article, the method comprising:
 assembling an absorbent article that comprises:
  a central region comprising absorbent material, the central region comprising a first end and a second end, wherein the first end and the second end are spaced at opposite ends of the central region along a longitudinal direction;

a front waist region located at the first end of the central region, wherein the front waist region extends in a lateral direction across a first end of the central region, wherein the lateral direction is generally transverse to the longitudinal direction; and a rear waist region located at the second end of the central region, wherein rear waist region extends in the lateral direction across the second end of the central region;

attaching a self-contained seal to the waist region during the assembling, wherein the seal comprises a compressed folded stack of resilient material contained within a sealed cavity such that the compressed folded stack comprises a first thickness, wherein the folded stack comprises a continuous length of the resilient material with two or more folds spaced apart across the rear waist region in the lateral direction and a segment of the resilient material extending in the lateral direction between each pair of folds at opposing ends of the segment; and forming an opening in the sealed cavity of the seal such that the compressed folded stack of resilient material expands to a second thickness greater than the first thickness as air enters the cavity.

2. A method according to claim 1, wherein forming the opening in the sealed cavity occurs before attaching the seal to the waist region.

3. A method according to claim 1, wherein forming the opening in the sealed cavity occurs after attaching the seal to the waist region.

4. A method according to claim 1, further comprising separating the seal from a web that comprises a plurality of seals contained in separate and discrete sealed cavities connected along a length of the web.

5. A method according to claim 1, wherein the segments in the folded stack of resilient material comprise different lengths as measured in the lateral direction.

6. A method of manufacturing an absorbent article, the method comprising:

assembling an absorbent article that comprises:

a central region comprising absorbent material, the central region comprising a first end and a second end, wherein the first end and the second end are spaced at opposite ends of the central region along a longitudinal direction;

a front waist region located at the first end of the central region, wherein the front waist region extends in a lateral direction across a first end of the central region, wherein the lateral direction is generally transverse to the longitudinal direction; and a rear waist region located at the second end of the central region, wherein rear waist region extends in the lateral direction across the second end of the central region;

attaching a self-contained seal to the waist region during the assembling, wherein the seal comprises resilient material gathered in a plurality of compressed pleats within a sealed cavity such that the seal comprises a first thickness, wherein the pleats comprise folds separating segments of the resilient material, and wherein the segments of each pleat are oriented generally transverse to a plane defined by the longitudinal and lateral directions; and forming an opening in the sealed cavity of the seal wherein the compressed pleats expand such that the seal comprises a second thickness greater than the first thickness as air enters the cavity.

7. A method according to claim 6, wherein forming the opening in the sealed cavity occurs before attaching the seal to the waist region.

8. A method according to claim 6, wherein forming the opening in the sealed cavity occurs after attaching the seal to the waist region.

9. A method according to claim 6, further comprising separating the seal from a web that comprises a plurality of seals contained in separate and discrete sealed cavities connected along a length of the web.

10. A method according to claim 6, wherein the segments in the plurality of pleats comprise different lengths between the folds.

11. A method of manufacturing an absorbent article, the method comprising:

assembling an absorbent article that comprises:

a central region comprising absorbent material, the central region comprising a first end and a second end, wherein the first end and the second end are spaced at opposite ends of the central region along a longitudinal direction;

a front waist region located at the first end of the central region, wherein the front waist region extends in a lateral direction across a first end of the central region, wherein the lateral direction is generally transverse to the longitudinal direction; and a rear waist region located at the second end of the central region, wherein rear waist region extends in the lateral direction across the second end of the central region;

attaching a self-contained seal to the waist region during the assembling, wherein the seal comprises a compressed stack of two or more discrete segments of resilient material contained within a sealed cavity such that the compressed stack comprises a first thickness, wherein the two or more discrete segments have different lengths along the lateral direction; and forming an opening in the sealed cavity of the seal such that the compressed stack of discrete segments of resilient material expands to a second thickness greater than the first thickness as air enters the cavity.

12. A method according to claim 11, wherein forming the opening in the sealed cavity occurs before attaching the seal to the waist region.

13. A method according to claim 11, wherein forming the opening in the sealed cavity occurs after attaching the seal to the waist region.

14. A method according to claim 11, further comprising separating the seal from a web that comprises a plurality of seals contained in separate and discrete sealed cavities connected along a length of the web.

15. A method according to claim 11, wherein, after forming an opening in the sealed cavity, the stack of two or more discrete segments of resilient material forms a sealing member that comprises a cross-sectional profile that is generally convex when taken in a z-direction plane that is transverse to a plane formed by the lateral and longitudinal directions and is also parallel to the lateral direction.

* * * * *